United States Patent [19]

Cormack et al.

[11] Patent Number: 5,529,916
[45] Date of Patent: Jun. 25, 1996

[54] LEUKOTRIENE A4 HYDROLASE FROM CANDIDA ALBICANS

[75] Inventors: Brendan P. Cormack, Saratoga; Stanley Falkow, Portola Valley, both of Calif.

[73] Assignee: Board of Trustees of the Leland Stanford Junior University, Stanford, Calif.

[21] Appl. No.: 332,838

[22] Filed: Nov. 1, 1994

[51] Int. Cl.$^6$ .............................. C12N 9/14; C12N 15/55
[52] U.S. Cl. ................ 435/195; 435/252.3; 435/254.22; 435/320.1; 536/23.2
[58] Field of Search ...................... 536/23.2; 435/320.1, 435/252.3, 255.1, 254.22, 252.33, 195

[56] References Cited

PUBLICATIONS

Orning, L., et al. "The Bifunctional Enzyme Leukotriene–$A_4$ Hydrolase Is an Arginine Aminopeptidase of High Efficiency and Specificity", *The Journal of Biological Chemistry*, 269(15):11269–11273 (1994).

Medina, J. F., et al., "Molecular Cloning and Expression of Mouse Leukotriene $A_4$ Hydrolase cDNA", *Biochemical and Biophysical Research Communications*, 176(3):1516–1524 (1991).

Makita, N., et al., "Molecular cloning and functional expression of rat leukotriene $A_4$ hydrolase using the polymerase chain reaction", *FEBS Letters*, 299(3):273–277 (1992).

Funk, C. D., et al., "Molecular cloning and amino acid sequence of leukotriene $A_4$ hydrolase", *Proc. Natl. Acad. Sci. USA*, 84:6677–6681 (1987).

Dahinden, C. A., et al., "Leukotriene $C_4$ production by murine mast cells: Evidence of a role for extracellular leukotriene $A_4$", *Proc. Natl. Acad. Sci. USA*, 82:6632–6636 (1985).

Claesson, H–E., et al., "Human endothelial cells stimulate leukotriene synthesis and convert granulocyte released leukortiene $A_4$ into leukotrienes $B_4$, $C_4$, $D_4$ and $E_4$", (1988), Env. J. Biochem 123(1), 93–100.

Odds, F. C., "*Candida* Species and Virulence", *ASM News*, 60(6):313–318 (1994).

Greenfield, R. A., "Host defense system intractions with *Candida*", *Journal of Medical and Veterinary Mycology*, 30:89–104 (1992).

Wetterholm, A., et al., "Recombinant mouse leukotriene $A_4$, hydrolase: a zinc metalloenzyme with dual enzymatic activities", *Biochemical and Biophysical Research Communications*, pp. 96–102 (1991), vol. 1082(2).

Brasch, J., et al., "*Candida albicans* in Glucose–free Media Contains Serum–independent Chemotactic Activity", *Acta Derm Venerol (Stockh)*, 72:1–3 (1992).

Thaler, M., et al., "Hepatic Candidiasis in Cancer Patients: The Evolving Picture of the Syndrome", *Annals of Internal Medicine*, 108:88–100 (1988).

McGee, J. E., et al., "Erythrocyte–neutrophil interactions: Formation of leukotriene $B_4$ by transcellular biosynthesis", *Proc. Natl. Acad. Sci. USA*, 83:1349–1353 (1986).

Castro, M., et al., "*Candida albicans* Stimulates Arachidonic Acid Liberation from Alveolar Macrophages through $\alpha$–Mannan and $\beta$–Glucan Cell Wall Components", *Infection and Immunity*, 62(8):3138–3145 (1994).

Parker, C. W., "Lipid Mediators Produced Through the Lipoxygenase Pathway", *Ann. Rev. Immuno.*, pp. 65–84 (1987).

Haeggström, J., "Cytosolic Liver Enzymes Catalyzing Hydrolysis of Leukotriene $A_4$ to Leukotriene $B_4$ and 5,6–Dihydroxyeicosatetraenoic Acid", *Methods in Enzymology*, 187:324–334 (1990).

*Primary Examiner*—Charles Patterson, Jr.
*Attorney, Agent, or Firm*—Flehr, Hohbach, Test, Albritton & Herbert

[57] ABSTRACT

The invention relates to yeast leukotriene $A_4$ hydrolase enzymes and nucleic acids.

7 Claims, 11 Drawing Sheets

```
Met Thr Arg Ala Ile Val Glu Ser Ile Lys Lys Arg Phe His Glu Leu
  1               5                  10                  15

Asp Pro Cys Thr Asn Ser Asn Tyr Ser Lys Phe Lys Val Ile His Thr
                 20                  25                  30

Asp Leu Thr Leu Thr Val Ser Phe Glu Ser Lys Thr Leu Asp Gly Thr
             35                  40                  45

Val Val Tyr Asp Leu Lys Asn Leu Asp Asn Ala Ser Glu Val Ile Leu
         50                  55                  60

Asp Thr Ser Ala Leu Lys Ile Lys Asn Ala Lys Val Asn Gly Lys Glu
 65                  70                  75                  80

Val Ser Phe Glu Leu Lys Pro Val Thr Pro Ile Tyr Gly Ala Pro Leu
             85                  90                  95

Arg Ile Pro Ile Asn Pro Asn Glu Ser Glu Ile Glu Val Glu Ile Ser
            100                 105                 110

Phe Thr Thr Asp Lys Cys Thr Ala Ile Gln Phe Ile Gln Gly Asp
            115                 120                 125

Thr Gly Pro Tyr Val Phe Ser Gln Cys Glu Ala Ile His Ala Arg Ser
        130                 135                 140

Leu Phe Pro Cys Phe Asp Thr Pro Ala Val Lys Ser Pro Tyr Lys Phe
        145                 150                 155                 160

Thr Gly His Ser Pro Ala Val Val Thr Met Ser Gly Arg Ala Gln Pro
        165                 170                 175

Thr Asp Glu Pro Asn Thr Tyr His Phe Asp Gln Pro Ile Pro Ile Pro
        180                 185                 190

Ser Tyr Leu Val Ser Ile Thr Ser Gly Asn Leu Leu Lys Ala Pro Ile
        195                 200                 205
```

FIG._1A

Gly Pro Arg Ser Asp Val Tyr Ser Glu Glu Pro Ser Leu Lys Lys Cys
210                         215                     220

Gln Trp Glu Phe Glu Lys Asp Met Glu Asn Phe Ile Gln Ile Ala Glu
225                         230                     235                 240

Lys Ile Val Phe Glu Tyr Glu Trp Ser Arg Phe Asp Ser Leu Val Leu
                245                     250                     255

Pro Ser Ser Phe Pro Tyr Gly Gly Met Gly Ile Pro Asn Met Thr Gln
                260                     265                     270

Leu Thr Pro Thr Leu Ile Ser Gly Asp Arg Thr Gln Thr Lys Val Met
        275                     280                     285

Ala His Glu Leu Ala His Ser Trp Ser Gly Asn Leu Val Thr Asn Ser
        290                     295                     300

Ser Trp Glu His Phe Trp Leu Asn Glu Gly Trp Thr Val Tyr Leu Glu
305                         310                     315                 320

Arg Arg Ile Ile Gly Ala Ile Ala Ala Ala Lys Glu Ala Lys Glu Glu Gly
                325                     330                     335

Arg Lys Asp Ala Glu Lys Tyr Gly Gln Val Arg His Phe Asn Met
                340                     345                     350

Ile Asn Gly Trp Asn Glu Leu Ala Asp Leu Asp Thr Cys Glu Thr Phe Asp Lys
355                         360                     365

Arg Tyr Thr Lys Leu Val Leu Asn Glu Asn Gly Asp Pro Asp Asp
370                         375                     380

Ser Phe Ser Arg Ile Pro Tyr Glu Lys Gly Phe Phe Leu Tyr His
385                         390                     395                 400

Leu Glu Thr Lys Leu Gly Gly Ile Lys Glu Phe Asp Pro Phe Ile Lys
                405                     410                     415

*FIG._1B*

Tyr Tyr Phe Asn Lys Phe Lys Tyr Gln Ser Leu Asn Thr Ala Gln Phe
420                          425                          430

Val Asp Thr Leu Tyr Glu Phe Tyr Glu Pro Lys Gly Lys Lys Ala Glu Ile
435                          440                          445

Leu Asp Asn Ile Asp Trp Glu Thr Trp Leu Phe Val Ser Gly Leu Pro
450                          455                          460

Glu Lys Pro Glu Phe Asp Val Thr Leu Ala Asn Gln Val Tyr Ala Leu
465                          470                          475                  480

Val Asp Lys Trp Val Ala Tyr Val Lys Asn Gly Gly Glu Leu Pro Gly
485                          490                          495

Asp Glu Thr Ala Asp Phe Glu Gly Gln Asp Met Leu Phe Leu Glu
500                          505                          510

Thr Leu Thr Glu Lys Phe Lys Thr Leu Asp Val Lys Pro Glu Ile Ile
515                          520                          525

Arg Leu Phe Pro Glu Ile Tyr Pro Lys Tyr Gly Ala Ser Lys Asn Gly
530                          535                          540

Glu Ile Ile Ser Arg Trp Asn Glu Leu Leu Ile Ser Tyr Gly Lys Tyr
545                          550                          555                  560

Ser Ser Gln Asp Thr Leu Val Gln Ser Phe Ala Ser Trp Leu Gly Thr
565                          570                          575

Ile Gly Arg Met Lys Tyr Val Arg Pro Gly Tyr Leu Leu Leu Arg Lys
580                          585                          590

Gly Ile Ser His Glu Phe Ala Leu Glu Val Phe Lys Lys Tyr Glu His
595                          600                          605

Ile Tyr His Pro Ile Cys Arg Thr Met Val Lys Lys Asp Leu Ser OCH
610                          615                          620

FIG._1C

```
Leu Lys Phe OCH Lys Phe Ala Ala Leu AMB OCH Phe Ser Phe Val Trp
625                 630                 635                 640
Phe Ile Glu Thr AMB Phe Lys Lys OCH Asp Arg Leu Cys Phe Tyr Asp
                645                 650                 655
Thr Val Val Leu Glu Ser Asp Gln His Pro Val Ser Gly Thr Leu Ser
                660                 665                 670
Arg Ser Asp Tyr Ser Trp Asp Ile Lys Lys Thr Lys Ile Glu Leu Ser
                675                 680                 685
Leu Asn Gly Val Cys Lys Val Glu
                690                 695
```

```
atg act aga gca att gtc gaa agc atc aaa aaa cgt ttc cac gaa ttg     48
met thr arg ala ile val glu ser ile lys lys arg phe his glu leu
 1               5                  10                  15 gat cca tgt acc aac tcg aat tat tcc aag ttc aaa gtt att cac aca     96
asp pro cys thr asn ser asn tyr ser lys phe lys val ile his thr
             20                  25                  30 gat ttg aca gtt tct ttt gaa tcc ttt gaa aca ttg gac gga aca        144
asp leu thr val ser phe glu ser phe glu thr leu asp gly thr
         35                  40                  45 gtt gtt tat gat ttg aaa aac ttg aat gca agt gaa gtt ata ttg        192
val val tyr asp leu lys asn leu asn ala ser glu val ile leu
     50                  55                  60 gat aca tct gca tta aaa ata aaA GCA AAT GCA AAA GGG AAA GAA        240
asp thr ser ala leu lys ile lys ala asn ala lys gly lys glu
 65                  70                  75                  80

GTG TCA TTT GAA TTG AAC CCC AAC GAA AGT ACA CCA GTT TAC TTG        288
val ser phe glu leu asn pro asn glu ser thr pro val tyr leu
                 85                  90                  95

AGA ATT CCT ATT AAC CCC ATT GCT ATT CAA TTT ATT GAA ATA TCT        336
arg ile pro ile asn pro ile ala ile gln phe ile glu ile ser
             100                 105                 110

TTC ACC ACG GAC AAA TGT ACT GAC AAA TTT CAA GGT GAC        384
phe thr thr asp lys cys thr ala ile gln phe ile gly asp
         115                 120                 125

ACT GGT CCA TAT GTT TTC TCC CAA TGT GAA GCC ATT CAT GCC AGA AGT    432
thr gly pro tyr val phe ser gln cys glu ala ile his ala arg ser
     130                 135                 140

TTG TTT CCA TGC TTT GAC ACA CCA GCA GTT AAA TCC TAC AAA TTC        480
leu phe pro cys phe asp thr pro ala val lys ser tyr lys phe
 145                 150                 155                 160
```

FIG._2A

```
ACA GGT CAT TCA CCA GCC GTG GTA ACC ATG TCA GGT AGA GCT CAA CCA    528
thr gly his ser pro ala val val thr met ser gly arg ala gln pro
            165                     170                 175

ACT GAC GAG CCA AAC ACA TAT CAT TTC GAT CAA CCA ATC CCT ATC CCA    576
thr asp glu pro asn thr tyr his phe asp gln pro ile pro ile pro
            180                     185                 190

TCT TAC TTG GTG TCA ATT ACT TCT GGT AAC TTG CTT AAA GCT CCA ATT    624
ser tyr leu val ser ile thr ser gly asn leu leu lys ala pro ile
            195                     200             205

GGT CCA AGA TCA GAT GTA TAT AGT GAA GAG CCA AGT TTG AAA AAA TGT    672
gly pro arg ser asp val tyr ser glu glu pro ser leu lys lys cys
            210                     215                 220

CAA TGG GAA TTT CCA GAA AAA GAT ATG GAG AAT TTT ATT CAA ATT GCT GAA    720
gln trp glu phe pro glu lys asp met glu asn phe ile gln ile ala glu
            225                 230                 235                 240

AAA aTA GTT TTC GAA TTC TAC GAA TGG TCT AGA TTT GAT TCC TTG GTA TTG    768
lys ile val phe glu phe tyr glu trp ser arg phe asp ser leu val leu
            245                 250                 255

CCA TCT AGT TTC CCA TAT GGA GGT ATG GAA ATC CCC AAT ATG ACT CAA    816
pro ser ser phe pro tyr gly gly met glu ile pro asn met thr gln
            260                     265                 270

TTG ACA CCA ACT TTA ATC AGT GGT GAT CGT ACT CAA ACC GTT AAA GTC ATG    864
leu thr pro thr leu ile ser gly asp arg thr gln thr val lys val met
            275                 280                 285

GCC CAC GAA TTG GCT CAT CAT TCC GGT AAT TTA ACC AAT TAT TTA AGT    912
ala his glu leu ala his his ser gly asn leu thr asn tyr asn ser
            290                     295                 300

TCC TGG GAA CAT TTC TGG CTC AAT GAA GGT TGG ACT GTA TAT TTA GAA    960
ser trp glu his phe trp leu asn glu gly trp thr val tyr leu glu
            305                     310                 315                 320
```

*FIG._2B*

```
AGA AGA ATT ATT GGT GCC ATT GCA GCA GCT GAA GCC AAA GAA GAA GGT      1008
arg arg ile ile gly ala ile ala ala ala glu ala lys glu glu gly
            325                         330                 335

AGA AAA GAT GCA GAG AAA TAT GGT GAA CAA GTG AGA CAT TTC AAT ATG      1056
arg lys asp ala glu lys tyr gly glu gln val arg his phe asn met
            340                         345                 350

ATT AAT GGA TGG AAT GAA TTA GCT GAT ACC TGT GAA ACA TTT GAT AAG      1104
ile asn gly trp asn glu leu ala asp thr cys glu thr phe asp lys
            355                         360                 365

AGA TAT ACC AAA TTG GTT TTG GAT TTA GAG AAT GGT GAT CCA GAT GAT      1152
arg tyr thr lys leu val leu asp leu glu asn gly asp pro asp asp
            370                         375                 380

TCG TTT TCT AGA ATT CCT TAT GAA AAA GGG TTT TTC TTC TTG TAT CAT      1200
ser phe ser arg ile pro tyr glu lys gly phe phe phe leu tyr his
            385                         390                 395                 400

TTA GAG ACT AAA TTG GGA GGT GGA ATA AAA TTG GAA TTT GAC CCA ATT AAA  1248
leu glu thr lys leu gly gly gly ile lys leu glu phe asp pro phe ile lys
            405                         410                 415

TAT TAT AAC TTC AAA AAA TTC AAa TAT CAA TCT TTG AAT CTA ACT GCT CAA TTT  1296
tyr tyr phe asn lys phe lys tyr gln ser leu asn thr ala gln phe
            420                         425                 430

GTT GAT ACT TTG TAT GAA TTC TAC GAA CCA TAC GAA AAA GGT AAA GCC GAA ATT  1344
val asp thr leu tyr glu phe tyr glu pro tyr glu lys gly lys ala glu ile
            435                         440                 445

TTG GAC AAC ATA GAT TGG ACT GAA TGG TTA TTT GTT TCC GGA CTT CCA      1392
leu asp asn ile asp trp thr glu trp leu phe val ser gly leu pro
            450                         455                 460

GAA AAG CCA GAA TTT GAT GTA ACT GTA ACT GCC AAT CAA GTA TAT GCT TTG      1440
glu lys pro glu phe asp phe asp val thr leu ala asn gln val tyr ala leu
            465                         470                 475                 480
```

FIG._2C

```
GTA GAT AAA TGG GTC GCT TAT GTC AAA AAT GGA GGT GAA CTT CCA GGT   1488
val asp lys trp val ala tyr val lys asn gly gly glu leu pro gly
            485                     490                     495

GAC GAA ACT GCC GAT TTT GAA GGT GAG CAA GAC ATG TTG TTT TTG GAA   1536
asp glu thr ala asp phe glu gly glu gln asp met leu phe leu glu
            500                     505                     510

ACC TTG ACA GAA AAA TTC AAG ACT CTT GAT GTT AAA CCT GAA ATT ATT   1584
thr leu thr glu lys phe lys thr leu asp val lys pro glu ile ile
            515                     520                     525

AGA TTC CCA GAA ATA TAC CCT AAA TAT GGA GCA AGt AAA AAT GGG GGT   1632
arg phe pro glu ile tyr pro lys tyr gly ala ser lys asn gly gly
            530                     535                     540

GAA ATT TCT CGT TGG AAC GAA TTG ATT AGT TAT GGT AAA TAC            1680
glu ile ser arg trp asn glu leu ile ser tyr gly lys tyr
            545                     550                     555                     560

TCA CAA GAT ACA TTG GTG CAA TCT TTT GCT AGT TGG TTG GGT ACA       1728
ser gln asp thr leu val gln ser phe ala ser trp leu gly thr
            565                     570                     575

ATT GGT CGT ATG AAA TAT GTC AGA CCT GGA TAT TTG TTG TTG AGG AAA   1776
ile gly arg met lys tyr val arg pro gly tyr leu leu leu arg lys
            580                     585                     590

GGC ATT AGT CAT GAA TTT GCT TTA GAG GTG TTT AAG AAG TAC GAG CAT   1824
gly ile ser his glu phe ala leu glu val phe lys lys tyr glu his
            595                     600                     605

ATT TAC CAC CCT ATT TGC AGA ACC ATG GTT AAG AAA GAT TTG AGT TAA   1872
ile tyr his pro ile cys arg thr met val lys lys asp leu ser OCH
            610                     615                     620

TTG AAG TTT TAA AAA TTT GCA GCT CTA TAG TAA TTT AGT TTT GTA TGG   1920
leu lys phe OCH lys phe ala ala leu AMB OCH phe ser phe val trp
            625                     630                     635                     640
```

```
TTT ATA GAA ACT TAG TTT AAA AAA TAA GAT AGG TTA TGT TTT Tac gac      1968
phe ile glu thr AMB phe lys lys OCH asp arg leu cys phe tyr asp
              645                             650                655 aca gtc gtc cta gaa tca gat caa cat cct gta agt ggc acg ttg agt      2016
thr val val leu glu ser asp gln his pro val ser gly thr leu ser
              660                             665                670 aga agt gat tat tca tgg gat att aag aaa aca aaa att gag ctc agt      2064
arg ser asp tyr ser trp asp ile lys lys thr lys ile glu leu ser
              675                             680                685 tta aat ggg gtt tgc aaa gta gag                                      2088
leu asn gly val cys lys val glu
              690                695
```

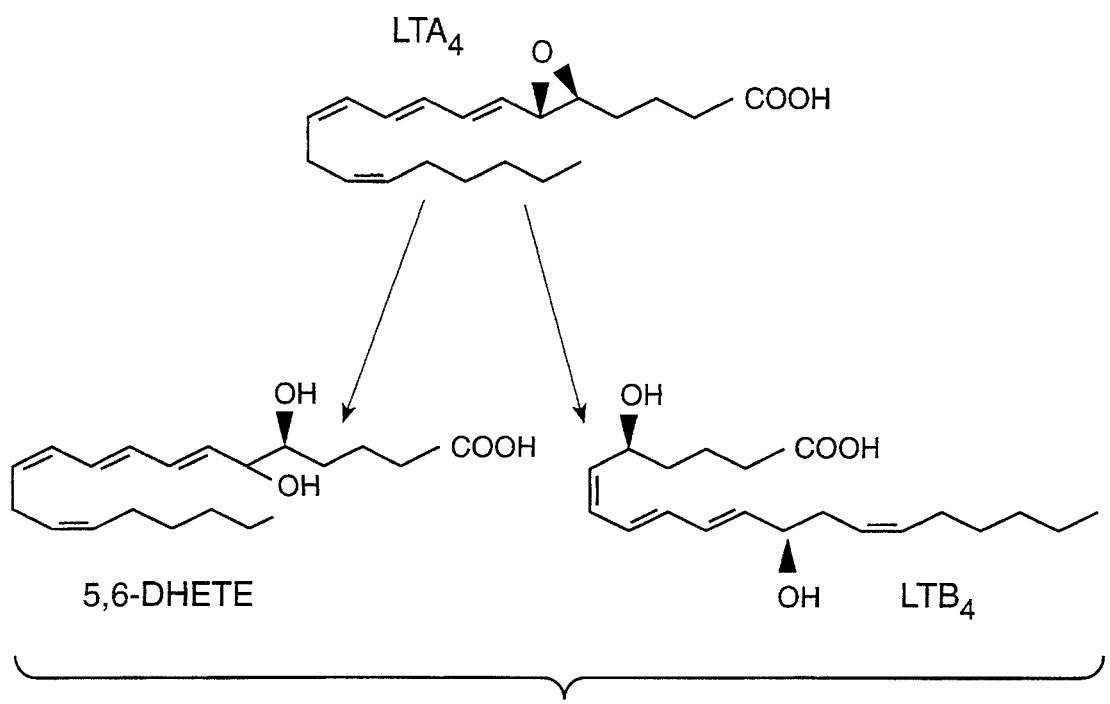
FIG._5
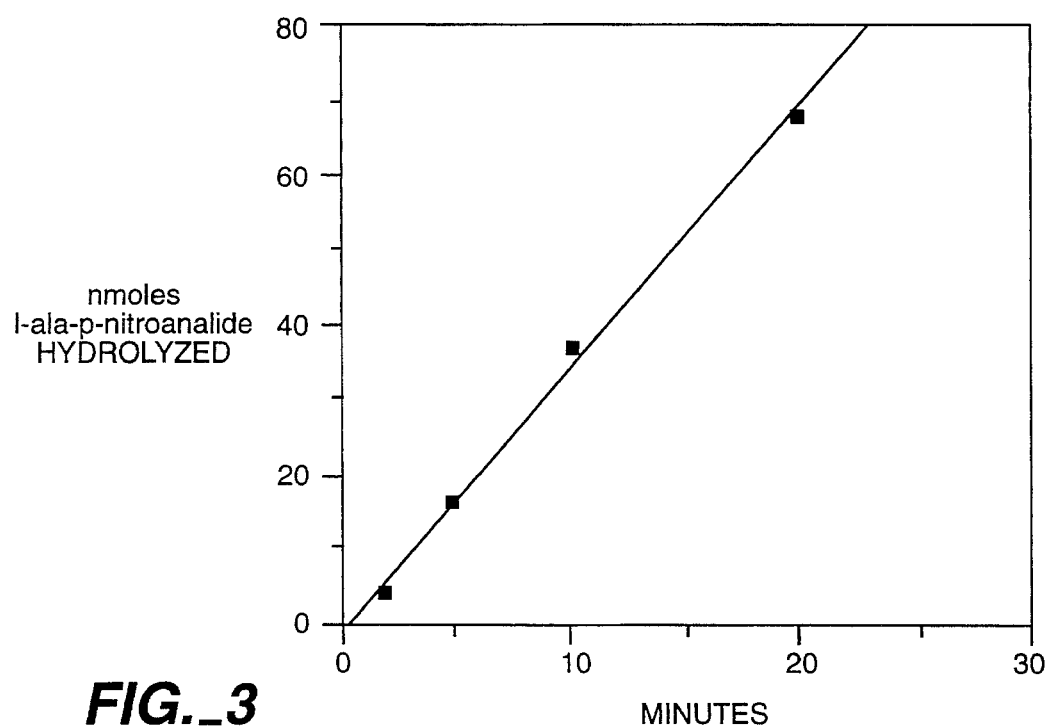
FIG._3

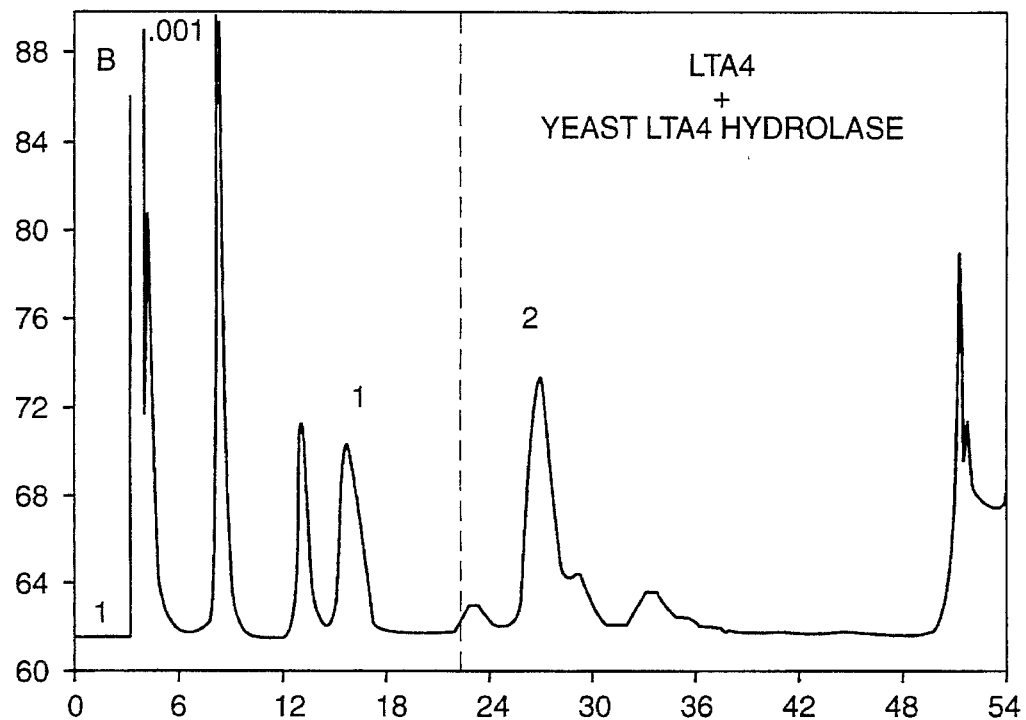
FIG._4A
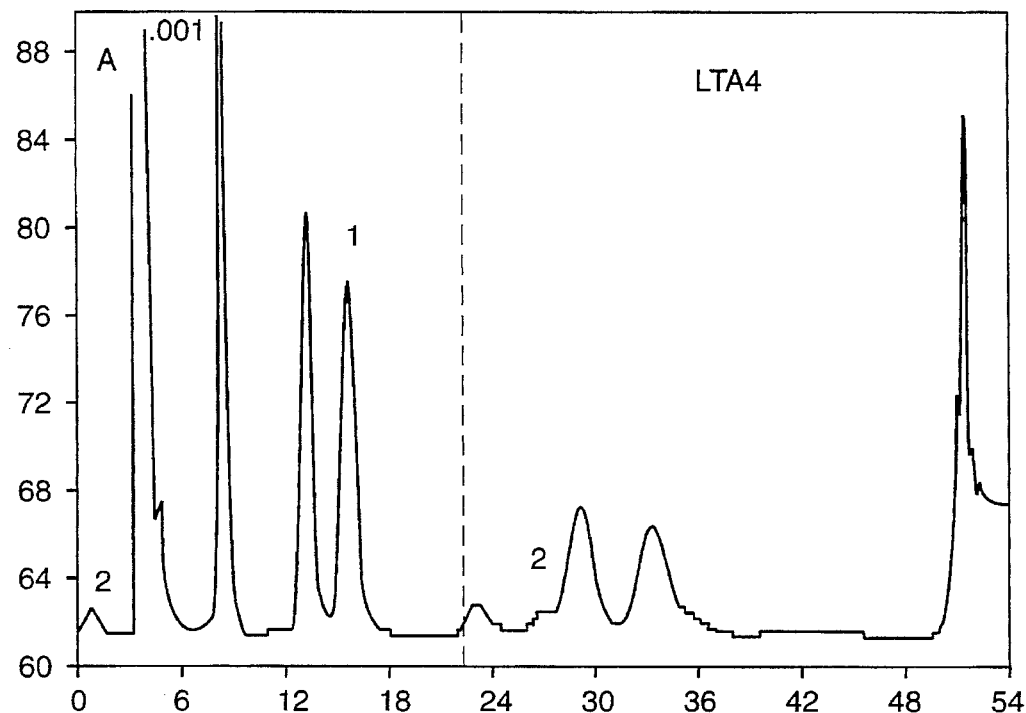
FIG._4B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2088 base pairs
        ( B ) TYPE: nucleic acid
        ( C ) STRANDEDNESS: double
        ( D ) TOPOLOGY: unknown ( i x ) FEATURE:
        ( A ) NAME/KEY: CDS
        ( B ) LOCATION: 1..1869

( x i ) SEQUENCE DESCRIPTION: SEQ ID NO:1:

```
ATG  ACT  AGA  GCA  ATT  GTC  GAA  AGC  ATC  AAA  AAA  CGT  TTC  CAC  GAA  TTG         48
Met  Thr  Arg  Ala  Ile  Val  Glu  Ser  Ile  Lys  Lys  Arg  Phe  His  Glu  Leu
 1                    5                   10                   15

GAT  CCA  TGT  ACC  AAC  TCG  AAT  TAT  TCC  AAG  TTC  AAA  GTT  ATT  CAC  ACA         96
Asp  Pro  Cys  Thr  Asn  Ser  Asn  Tyr  Ser  Lys  Phe  Lys  Val  Ile  His  Thr
                20                   25                        30

GAT  TTG  ACT  TTG  ACA  GTT  TCT  TTT  GAA  TCC  AAA  ACA  TTG  GAC  GGA  ACA        144
Asp  Leu  Thr  Leu  Thr  Val  Ser  Phe  Glu  Ser  Lys  Thr  Leu  Asp  Gly  Thr
           35                        40                        45

GTT  GTT  TAT  GAT  TTG  AAA  AAC  TTG  GAT  AAT  GCA  AGT  GAA  GTT  ATA  TTG        192
Val  Val  Tyr  Asp  Leu  Lys  Asn  Leu  Asp  Asn  Ala  Ser  Glu  Val  Ile  Leu
      50                        55                        60

GAT  ACA  TCT  GCA  TTA  AAA  ATA  AAA  AAT  GCA  AAA  GTC  AAC  GGG  AAA  GAA        240
Asp  Thr  Ser  Ala  Leu  Lys  Ile  Lys  Asn  Ala  Lys  Val  Asn  Gly  Lys  Glu
 65                   70                        75                        80

GTG  TCA  TTT  GAA  TTG  AAA  CCA  GTT  ACA  CCA  ATT  TAC  GGA  GCA  CCA  TTG        288
Val  Ser  Phe  Glu  Leu  Lys  Pro  Val  Thr  Pro  Ile  Tyr  Gly  Ala  Pro  Leu
```

|  |  |  |  |  |  |  |  |  |  |  |  |  |  |  |  |  |
|--|--|--|--|--|--|--|--|--|--|--|--|--|--|--|--|--|
|  |  |  |  | 85 |  |  |  | 90 |  |  |  | 95 |  |  |  |  |
| AGA | ATT | CCT | ATT | AAC | CCC | AAC | GAA | AGT | GAA | ATT | GAA | GTT | GAA | ATA | TCT | 336 |
| Arg | Ile | Pro | Ile<br>100 | Asn | Pro | Asn | Glu | Ser<br>105 | Glu | Ile | Glu | Val<br>110 | Glu | Ile | Ser |  |
| TTC | ACC | ACC | ACG | GAC | AAA | TGT | ACT | GCT | ATT | CAA | TTT | ATT | CAA | GGT | GAC | 384 |
| Phe | Thr | Thr<br>115 | Thr | Asp | Lys | Cys | Thr<br>120 | Ala | Ile | Gln | Phe | Ile<br>125 | Gln | Gly | Asp |  |
| ACT | GGT | CCA | TAT | GTT | TTC | TCC | CAA | TGT | GAA | GCC | ATT | CAT | GCC | AGA | AGT | 432 |
| Thr | Gly<br>130 | Pro | Tyr | Val | Phe | Ser<br>135 | Gln | Cys | Glu | Ala | Ile<br>140 | His | Ala | Arg | Ser |  |
| TTG | TTT | CCA | TGC | TTT | GAC | ACA | CCA | GCA | GTT | AAA | TCC | CCT | TAC | AAA | TTC | 480 |
| Leu<br>145 | Phe | Pro | Cys | Phe | Asp<br>150 | Thr | Pro | Ala | Val | Lys<br>155 | Ser | Pro | Tyr | Lys | Phe<br>160 |  |
| ACA | GGT | CAT | TCA | CCA | GCC | GTG | GTA | ACC | ATG | TCA | GGT | AGA | GCT | CAA | CCA | 528 |
| Thr | Gly | His | Ser<br>165 | Pro | Ala | Val | Val | Thr | Met<br>170 | Ser | Gly | Arg | Ala | Gln<br>175 | Pro |  |
| ACT | GAC | GAG | CCA | AAC | ACA | TAT | CAT | TTC | GAT | CAA | CCA | ATC | CCT | ATC | CCA | 576 |
| Thr | Asp | Glu | Pro<br>180 | Asn | Thr | Tyr | His | Phe<br>185 | Asp | Gln | Pro | Ile | Pro<br>190 | Ile | Pro |  |
| TCT | TAC | TTG | GTG | TCA | ATT | ACT | TCT | GGT | AAC | TTG | CTT | AAA | GCT | CCA | ATT | 624 |
| Ser | Tyr | Leu | Val | Ser<br>195 | Ile | Thr | Ser | Gly | Asn<br>200 | Leu | Leu | Lys | Ala | Pro<br>205 | Ile |  |
| GGT | CCA | AGA | TCA | GAT | GTA | TAT | AGT | GAA | GAG | CCA | AGT | TTG | AAA | AAA | TGT | 672 |
| Gly | Pro<br>210 | Arg | Ser | Asp | Val | Tyr<br>215 | Ser | Glu | Glu | Pro | Ser<br>220 | Leu | Lys | Lys | Cys |  |
| CAA | TGG | GAA | TTT | GAA | AAA | GAT | ATG | GAG | AAT | TTT | ATT | CAA | ATT | GCT | GAA | 720 |
| Gln<br>225 | Trp | Glu | Phe | Glu | Lys<br>230 | Asp | Met | Glu | Asn | Phe<br>235 | Ile | Gln | Ile | Ala | Glu<br>240 |  |
| AAA | ATA | GTT | TTC | GAA | TAC | GAA | TGG | TCT | AGA | TTT | GAT | TCC | TTG | GTA | TTG | 768 |
| Lys | Ile | Val | Phe | Glu<br>245 | Tyr | Glu | Trp | Ser | Arg<br>250 | Phe | Asp | Ser | Leu | Val<br>255 | Leu |  |
| CCA | TCT | AGT | TTC | CCA | TAT | GGA | GGT | ATG | GAA | ATC | CCC | AAT | ATG | ACT | CAA | 816 |
| Pro | Ser | Ser | Phe<br>260 | Pro | Tyr | Gly | Gly | Met<br>265 | Glu | Ile | Pro | Asn | Met<br>270 | Thr | Gln |  |
| TTG | ACA | CCA | ACT | TTA | ATC | AGT | GGT | GAT | CGT | ACT | CAA | ACC | AAA | GTC | ATG | 864 |
| Leu | Thr | Pro<br>275 | Thr | Leu | Ile | Ser | Gly<br>280 | Asp | Arg | Thr | Gln | Thr<br>285 | Lys | Val | Met |  |
| GCC | CAC | GAA | TTG | GCT | CAT | TCA | TGG | TCC | GGT | AAT | TTA | GTT | ACC | AAT | AGT | 912 |
| Ala | His<br>290 | Glu | Leu | Ala | His | Ser<br>295 | Trp | Ser | Gly | Asn | Leu<br>300 | Val | Thr | Asn | Ser |  |
| TCC | TGG | GAA | CAT | TTC | TGG | CTC | AAT | GAA | GGT | TGG | ACT | GTA | TAT | TTA | GAA | 960 |
| Ser<br>305 | Trp | Glu | His | Phe | Trp<br>310 | Leu | Asn | Glu | Gly | Trp<br>315 | Thr | Val | Tyr | Leu | Glu<br>320 |  |
| AGA | AGA | ATT | ATT | GGT | GCC | ATT | GCA | GCA | GCT | GAA | GCC | AAA | GAA | GAA | GGT | 1008 |
| Arg | Arg | Ile | Ile | Gly<br>325 | Ala | Ile | Ala | Ala | Ala<br>330 | Glu | Ala | Lys | Glu | Glu<br>335 | Gly |  |
| AGA | AAA | GAT | GCA | GAG | AAA | TAT | GGT | GAA | CAA | GTG | AGA | CAT | TTC | AAT | ATG | 1056 |
| Arg | Lys | Asp | Ala<br>340 | Glu | Lys | Tyr | Gly | Glu<br>345 | Gln | Val | Arg | His | Phe<br>350 | Asn | Met |  |
| ATT | AAT | GGA | TGG | AAT | GAA | TTA | GCT | GAT | ACC | TGT | GAA | ACA | TTT | GAT | AAG | 1104 |
| Ile | Asn | Gly | Trp<br>355 | Asn | Glu | Leu | Ala | Asp<br>360 | Thr | Cys | Glu | Thr | Phe<br>365 | Asp | Lys |  |
| AGA | TAT | ACC | AAA | TTG | GTT | TTG | GAT | TTA | GAG | AAT | GGT | GAT | CCA | GAT | GAT | 1152 |
| Arg | Tyr | Thr<br>370 | Lys | Leu | Val | Leu | Asp<br>375 | Leu | Glu | Asn | Gly | Asp<br>380 | Pro | Asp | Asp |  |
| TCG | TTT | TCT | AGA | ATT | CCT | TAT | GAA | AAA | GGG | TTT | TTC | TTG | TAT | CAT | | 1200 |
| Ser<br>385 | Phe | Ser | Arg | Ile | Pro<br>390 | Tyr | Glu | Lys | Gly | Phe<br>395 | Phe | Phe | Leu | Tyr | His<br>400 |  |
| TTA | GAG | ACT | AAA | TTG | GGA | GGT | ATA | AAA | GAA | TTT | GAC | CCA | TTT | ATT | AAA | 1248 |
| Leu | Glu | Thr | Lys | Leu | Gly | Gly | Ile | Lys | Glu | Phe | Asp | Pro | Phe | Ile | Lys |  |

```
                            405                          410                          415
TAT  TAT  TTT  AAC  AAA  TTC  AAA  TAT  CAA  TCT  TTG  AAT  ACT  GCT  CAA  TTT        1296
Tyr  Tyr  Phe  Asn  Lys  Phe  Lys  Tyr  Gln  Ser  Leu  Asn  Thr  Ala  Gln  Phe
               420                     425                    430

GTT  GAT  ACT  TTG  TAT  GAA  TTC  TAC  GAA  CCA  AAA  GGT  AAA  GCC  GAA  ATT        1344
Val  Asp  Thr  Leu  Tyr  Glu  Phe  Tyr  Glu  Pro  Lys  Gly  Lys  Ala  Glu  Ile
          435                     440                         445

TTG  GAC  AAC  ATA  GAT  TGG  GAA  ACT  TGG  TTA  TTT  GTT  TCC  GGA  CTT  CCA        1392
Leu  Asp  Asn  Ile  Asp  Trp  Glu  Thr  Trp  Leu  Phe  Val  Ser  Gly  Leu  Pro
     450                          455                    460

GAA  AAG  CCA  GAA  TTT  GAT  GTA  ACT  TTG  GCC  AAT  CAA  GTA  TAT  GCT  TTG        1440
Glu  Lys  Pro  Glu  Phe  Asp  Val  Thr  Leu  Ala  Asn  Gln  Val  Tyr  Ala  Leu
465                      470                    475                         480

GTA  GAT  AAA  TGG  GTC  GCT  TAT  GTC  AAA  AAT  GGA  GGT  GAA  CTT  CCA  GGT        1488
Val  Asp  Lys  Trp  Val  Ala  Tyr  Val  Lys  Asn  Gly  Gly  Glu  Leu  Pro  Gly
               485                     490                         495

GAC  GAA  ACT  GCC  GAT  TTT  GAA  GGT  GAG  CAA  GAC  ATG  TTG  TTT  TTG  GAA        1536
Asp  Glu  Thr  Ala  Asp  Phe  Glu  Gly  Glu  Gln  Asp  Met  Leu  Phe  Leu  Glu
          500                          505                    510

ACC  TTG  ACA  GAA  AAA  TTC  AAG  ACT  CTT  GAT  GTT  AAA  CCT  GAA  ATT  ATT        1584
Thr  Leu  Thr  Glu  Lys  Phe  Lys  Thr  Leu  Asp  Val  Lys  Pro  Glu  Ile  Ile
          515                          520                    525

AGA  TTG  TTC  CCA  GAA  ATA  TAC  CCT  AAA  TAT  GGA  GCA  AGT  AAA  AAT  GGG        1632
Arg  Leu  Phe  Pro  Glu  Ile  Tyr  Pro  Lys  Tyr  Gly  Ala  Ser  Lys  Asn  Gly
     530                          535                    540

GAA  ATT  ATT  TCT  CGT  TGG  AAC  GAA  TTG  TTG  ATT  AGT  TAT  GGT  AAA  TAC        1680
Glu  Ile  Ile  Ser  Arg  Trp  Asn  Glu  Leu  Leu  Ile  Ser  Tyr  Gly  Lys  Tyr
545                      550                         555                    560

TCA  TCC  CAA  GAT  ACA  TTG  GTG  CAA  TCT  TTT  GCT  AGT  TGG  TTG  GGT  ACA        1728
Ser  Ser  Gln  Asp  Thr  Leu  Val  Gln  Ser  Phe  Ala  Ser  Trp  Leu  Gly  Thr
               565                     570                         575

ATT  GGT  CGT  ATG  AAA  TAT  GTC  AGA  CCT  GGA  TAT  TTG  TTG  TTG  AGG  AAA        1776
Ile  Gly  Arg  Met  Lys  Tyr  Val  Arg  Pro  Gly  Tyr  Leu  Leu  Leu  Arg  Lys
               580                     585                         590

GGC  ATT  AGT  CAT  GAA  TTT  GCT  TTA  GAG  GTG  TTT  AAG  AAG  TAC  GAG  CAT        1824
Gly  Ile  Ser  His  Glu  Phe  Ala  Leu  Glu  Val  Phe  Lys  Lys  Tyr  Glu  His
          595                          600                    605

ATT  TAC  CAC  CCT  ATT  TGC  AGA  ACC  ATG  GTT  AAG  AAA  GAT  TTG  AGT             1869
Ile  Tyr  His  Pro  Ile  Cys  Arg  Thr  Met  Val  Lys  Lys  Asp  Leu  Ser
     610                     615                    620

TAATTGAAGT  TTTAAAAATT  TGCAGCTCTA  TAGTAATTTA  GTTTTGTATG  GTTTATAGAA             1929

ACTTAGTTTA  AAAAATAAGA  TAGGTTATGT  TTTTACGACA  CAGTCGTCCT  AGAATCAGAT             1989

CAACATCCTG  TAAGTGGCAC  GTTGAGTAGA  AGTGATTATT  CATGGGATAT  TAAGAAAACA             2049

AAAATTGAGC  TCAGTTTAAA  TGGGGTTTGC  AAAGTAGAG                                      2088
```

( 2 ) INFORMATION FOR SEQ ID NO:2:

( i ) SEQUENCE CHARACTERISTICS:
        ( A ) LENGTH: 623 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Arg  Ala  Ile  Val  Glu  Ser  Ile  Lys  Lys  Arg  Phe  His  Glu  Leu
 1               5                         10                        15

Asp  Pro  Cys  Thr  Asn  Ser  Asn  Tyr  Ser  Lys  Phe  Lys  Val  Ile  His  Thr
               20                        25                        30
```

```
Asp Leu Thr Leu Thr Val Ser Phe Glu Ser Lys Thr Leu Asp Gly Thr
         35                  40                  45

Val Val Tyr Asp Leu Lys Asn Leu Asp Asn Ala Ser Glu Val Ile Leu
     50                  55                  60

Asp Thr Ser Ala Leu Lys Ile Lys Asn Ala Lys Val Asn Gly Lys Glu
 65                  70                  75                  80

Val Ser Phe Glu Leu Lys Pro Val Thr Pro Ile Tyr Gly Ala Pro Leu
                 85                  90                  95

Arg Ile Pro Ile Asn Pro Asn Glu Ser Glu Ile Glu Val Glu Ile Ser
             100                 105                 110

Phe Thr Thr Thr Asp Lys Cys Thr Ala Ile Gln Phe Ile Gln Gly Asp
         115                 120                 125

Thr Gly Pro Tyr Val Phe Ser Gln Cys Glu Ala Ile His Ala Arg Ser
     130                 135                 140

Leu Phe Pro Cys Phe Asp Thr Pro Ala Val Lys Ser Pro Tyr Lys Phe
145                 150                 155                 160

Thr Gly His Ser Pro Ala Val Val Thr Met Ser Gly Arg Ala Gln Pro
                 165                 170                 175

Thr Asp Glu Pro Asn Thr Tyr His Phe Asp Gln Pro Ile Pro Ile Pro
             180                 185                 190

Ser Tyr Leu Val Ser Ile Thr Ser Gly Asn Leu Leu Lys Ala Pro Ile
         195                 200                 205

Gly Pro Arg Ser Asp Val Tyr Ser Glu Glu Pro Ser Leu Lys Lys Cys
     210                 215                 220

Gln Trp Glu Phe Glu Lys Asp Met Glu Asn Phe Ile Gln Ile Ala Glu
225                 230                 235                 240

Lys Ile Val Phe Glu Tyr Glu Trp Ser Arg Phe Asp Ser Leu Val Leu
                 245                 250                 255

Pro Ser Ser Phe Pro Tyr Gly Gly Met Glu Ile Pro Asn Met Thr Gln
             260                 265                 270

Leu Thr Pro Thr Leu Ile Ser Gly Asp Arg Thr Gln Thr Lys Val Met
         275                 280                 285

Ala His Glu Leu Ala His Ser Trp Ser Gly Asn Leu Val Thr Asn Ser
     290                 295                 300

Ser Trp Glu His Phe Trp Leu Asn Glu Gly Trp Thr Val Tyr Leu Glu
305                 310                 315                 320

Arg Arg Ile Ile Gly Ala Ile Ala Ala Ala Glu Ala Lys Glu Glu Gly
                 325                 330                 335

Arg Lys Asp Ala Glu Lys Tyr Gly Glu Gln Val Arg His Phe Asn Met
             340                 345                 350

Ile Asn Gly Trp Asn Glu Leu Ala Asp Thr Cys Glu Thr Phe Asp Lys
         355                 360                 365

Arg Tyr Thr Lys Leu Val Leu Asp Leu Glu Asn Gly Asp Pro Asp Asp
     370                 375                 380

Ser Phe Ser Arg Ile Pro Tyr Glu Lys Gly Phe Phe Phe Leu Tyr His
385                 390                 395                 400

Leu Glu Thr Lys Leu Gly Gly Ile Glu Lys Phe Asp Pro Phe Ile Lys
                 405                 410                 415

Tyr Tyr Phe Asn Lys Phe Lys Tyr Gln Ser Leu Asn Thr Ala Gln Phe
             420                 425                 430

Val Asp Thr Leu Tyr Glu Phe Tyr Glu Pro Lys Gly Lys Ala Glu Ile
         435                 440                 445

Leu Asp Asn Ile Asp Trp Glu Thr Trp Leu Phe Val Ser Gly Leu Pro
     450                 455                 460
```

| | | | | | | | | | | | | | | | |
|---|---|---|---|---|---|---|---|---|---|---|---|---|---|---|---|
| Glu 465 | Lys | Pro | Glu | Phe | Asp 470 | Val | Thr | Leu | Ala | Asn 475 | Gln | Val | Tyr | Ala | Leu 480 |
| Val | Asp | Lys | Trp | Val 485 | Ala | Tyr | Val | Lys | Asn 490 | Gly | Gly | Glu | Leu | Pro 495 | Gly |
| Asp | Glu | Thr | Ala 500 | Asp | Phe | Glu | Gly | Glu 505 | Gln | Asp | Met | Leu | Phe 510 | Leu | Glu |
| Thr | Leu | Thr 515 | Glu | Lys | Phe | Lys | Thr 520 | Leu | Asp | Val | Lys | Pro 525 | Glu | Ile | Ile |
| Arg | Leu 530 | Phe | Pro | Glu | Ile | Tyr 535 | Pro | Lys | Tyr | Gly | Ala 540 | Ser | Lys | Asn | Gly |
| Glu 545 | Ile | Ile | Ser | Arg | Trp 550 | Asn | Glu | Leu | Leu | Ile 555 | Ser | Tyr | Gly | Lys | Tyr 560 |
| Ser | Ser | Gln | Asp | Thr 565 | Leu | Val | Gln | Ser | Phe 570 | Ala | Ser | Trp | Leu | Gly 575 | Thr |
| Ile | Gly | Arg | Met 580 | Lys | Tyr | Val | Arg | Pro 585 | Gly | Tyr | Leu | Leu | Leu 590 | Arg | Lys |
| Gly | Ile | Ser 595 | His | Glu | Phe | Ala | Leu 600 | Glu | Val | Phe | Lys | Lys 605 | Tyr | Glu | His |
| Ile | Tyr 610 | His | Pro | Ile | Cys | Arg 615 | Thr | Met | Val | Lys | Lys 620 | Asp | Leu | Ser | |

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTTTTTTTTT TTAG 14

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TAGCATATGG AG 12

LEUKOTRIENE A4 HYDROLASE FROM CANDIDA ALBICANS

FIELD OF THE INVENTION

The invention relates to yeast leukotriene A4 hydrolase enzymes and nucleic acids.

BACKGROUND OF THE INVENTION

*Candida albicans* is one of the most significant fungal/yeast pathogens in man. The organism is a normal commensal in humans, found in the gastrointestinal tract and vagina. In immunocompetent individuals Candida can colonize the oral mucosal surface (thrush) and the vaginal epithelia (Candida vaginitis). Lymphocytes are important in protection against these superficial infections consistent with the fact that HIV infected individuals are highly susceptible to mucocutaneous candidiasis.

To do more than colonize the epithelial surface, Candida need an immunocompromised host. Candidiasis is the most frequently encountered systemic fungal infection in the compromised host. For example, disseminated candidiasis occurs in 11–27% of patients with protracted neutropenia from acute leukemia or bone marrow transplantation, resulting in mortality which may approach 95%. Human immunodeficiency virus-infected patients commonly get chronic, superficial Candida infections. Increasingly, Candida infections are encountered in seriously ill hospitalized patients without classic immunocompromising diseases. For reviews, see Greenfield, J. of Med. and Vet. Mycology 30:89–104 (1992); and Odds, ASM News 60(6):313 (1994).

There is little humoral component in the immune response to systemic *C. albicans* infection, and protection is thought to be largely at the level of inflammation, with recruitment of neutrophils, monocytes and eosinophils to the site of infection.

Current therapy choices for fungal pathogens are limited largely to azole compounds such as clotrimazole or fluconazole, and in the case of deep systemic infections, to the highly toxic amphotericin B and 5-fluorocytosine. In addition, diagnosis of systemic candidiasis is difficult, with blood cultures often negative in spite of continued deep organ infection.

Acute inflammatory reactions are characterized by a series of vascular events including neutrophil adherence to endothelium, neutrophil diapedesis, and vasoconstriction accompanied by increased vascular permeability. Leukotrienes are important lipid derived mediators of inflammation in humans, frequently acting as powerful proinflammatory agents. Of the leukotrienes, Leukotriene $B_4$ ($LTB_4$, (5S, 12R)-5,12-dihydroxy-6,14-cis-8,10-trans-icosatetraenoic acid) is a major mediator of leukocyte activation. Its effects include stimulation of cell aggregation, lysosomal enzyme release, and nondirected migration and chemotaxis. It is responsible for local recruitment of neutrophils to sites of inflammation, and is thought to be important in modulation of T lymphocyte function.

$LTB_4$ is particularly potent in inducing leukocyte aggregation; it produces responses at concentrations in the nanomolar or high picomolar range.

The leukotrienes are synthesized by the action of lipoxygenase enzymes on arachidonic acid, which is a $C_{20}$ fatty acid with double bonds at the 5–6, 8–9, 11–12, and 14–15 positions. Thus arachidonic acid is considered the precursor of all the leukotrienes.

Specifically, it appears that $LTB_4$ is made by the conversion of $LTA_4$, an unstable intermediate, to LTB4 by $LTA_4$ hydrolase. $LTA_4$ hydrolase has been cloned from humans (Funk et al., Proc. Natl. Acad. Sci. USA 84(19):6677–81 (1987)); rats (Mkita et al., FEBS Lett. 299(3):273–7 (1992); guinea pigs (unpublished; Genbank) and mice (Medina et al., Biochem. biophys. Res. Comm. 176(3):1516–24 (1991)). The mouse $LTA_4$ hydrolase enzyme has been shown to be a zinc metalloenzyme with dual enzymatic activities, a $LTA_4$ hydrolase activity and an aminopeptidase activity (Wetterholm et al., Biochim. et Biophys. Acta 1080(2):96–102 (1991); Orning et al., J. Biol. Chem. 269(15):11269–73 (1994)). The human $LTA_4$ hydrolase enzyme has been shown to work both intracellularly and transcellularly to convert $LTA_4$ to $LTB_4$ (McGee et al., Proc. Natl. Acad. Sci. USA 83:1349–1353 (1986)).

It is an object of the present invention to provide for recombinant yeast $LTA_4$ hydrolase proteins and variants thereof, and methods to produce useful quantities of these yeast $LTA_4$ hydrolase proteins using recombinant DNA techniques.

It is a further object of the invention to provide recombinant nucleic acids encoding yeast $LTA_4$ hydrolase proteins, and expression vectors and host cells containing the nucleic acid encoding the yeast $LTA_4$ hydrolase protein.

An additional object of the invention is to provide monoclonal antibodies for the diagnosis of Candida infection.

A further object of the invention is to provide methods for producing the yeast $LTA_4$ hydrolase proteins, and vaccines comprising the yeast $LTA_4$ hydrolase proteins of the present invention.

Another object of the invention is to provide methods and compositions for screening for $LTA_4$ hydrolase inhibitors.

SUMMARY OF THE INVENTION

In accordance with the foregoing objects, the present invention provides recombinant yeast $LTA_4$ hydrolase proteins.

An additional aspect provides recombinant nucleic acids encoding yeast $LTA_4$ hydrolase proteins.

In another aspect, the invention provides expression vectors comprising transcriptional and translational regulatory DNA operably linked to DNA encoding a yeast $LTA_4$ hydrolase, and host cells transformed with these expression vectors.

Yet another aspect provides methods for producing yeast $LTA_4$ hydrolase proteins comprising culturing a host cell transformed with an expression vector comprising a nucleic acid encoding a yeast $LTA_4$ hydrolase protein. The nucleic acid is then expressed to produce the protein.

In an additional aspect, the invention provides monoclonal antibodies to a yeast $LTA_4$ hydrolase protein.

BRIEF DESCRIPTION OF THE DRAWINGS

FIGS. 1A–1D depict the amino acid sequence (SEQ ID NO:2) of the yeast $LTA_4$ hydrolase protein, using standard single letter amino acid abbreviations.

FIGS. 2A–2E depict the nucleic acid (SEQ ID NO:1) and amino acid (SEQ ID NO:2) sequence of the yeast $LTA_4$ hydrolase protein.

FIG. 3 depicts the aminopeptidase activity of the yeast LTA$_4$ hydrolase protein as outlined in the Examples.

FIGS. 4A and 4B depict the chromatograms of the LTA$_4$ hydrolysis reaction in the presence and absence of the yeast LTA$_4$ hydrolase protein. FIG. 1A shows the hydrolysis of LTA$_4$ by water in the absence of enzyme, showing the range of non-enzymatic hydrolysis products. FIG. 4B depicts the products from hydrolysis of LTA$_4$ by the yeast LTA$_4$ hydrolase protein. There is a predominant novel product (peak 2 eluting at 27 minutes) which coelutes with 5,6, diHETE. There is also a small shoulder on peak 1 (eluting at 17 minutes) which coelutes with LTB$_4$.

FIG. 5 schematically depicts the conversion of LTA$_4$ to LTB$_4$ and 5,6 diHETE.

DETAILED DESCRIPTION OF THE INVENTION

The invention is based on the discovery that *Candida albicans* expresses a gene functionally and structurally similar to mammalian LTA$_4$ hydrolase. The presence of a LTA$_4$ hydrolase gene in the *Candida albicans* genome is particularly interesting, since *C. albicans* lacks arachidonic acid, the precursor of all leukotrienes; this suggests that the Candida LTA$_4$ hydrolase enzyme is likely to be important in the interaction of the yeast with mammalian hosts.

Of particular significance in the present invention is the fact that the yeast LTA$_4$ hydrolase enzyme, rather than converting the LTA$_4$ to LTB$_4$, as is known for the mammalian enzymes, converts the majority of the LTA$_4$ to what has putatively identified as a 5,6 dihydroxy fatty acid (5,6-dihydroxy-7,9,11,14-eicoatetraenoic acid (5,6, diHETE)), a much less potent leukotriene.

In addition, similar to the mouse enzyme, the yeast LTA$_4$ hydrolase enzyme appears to have aminopeptidase activity.

Without being bound by theory, it is possible that the yeast LTA$_4$ hydrolase enzyme is made by *C. albicans* to compete with the host LTA$_4$ hydrolase to reduce the production of LTB$_4$, reducing inflammation. In so doing, the yeast LTA$_4$ hydrolase enzyme thus prevents or reduces the production of the proinflammatory LTB$_4$ by channeling the conversion of LTA$_4$ to 5,6, diHETE. This reduces the host immune response and allows for pathogenic growth of the Candida organism. This proposed role in pathogenesis is entirely consistent with the clinical presentation of systemic candidiasis, whose features include the formation of macroabscesses on the major organs, particularly the liver, kidney and spleen. The persistence of such abscesses could be directly related to the suppression of a normal inflammation response by the colonized Candida. It is also possible that the specific product(s) of the yeast LTA$_4$ hydrolase enzyme has, like LTB$_4$, a direct effect in modulating leukocyte function. Such a direct effect would be consistent, for example, with the clinical presentation of vaginal candidiasis, in which there is a down regulation of cell mediated immunity.

In addition, it is possible that yeast LTA$_4$ hydrolase expression correlates in some way to the switch from a commensal state to a pathogenic state in Candida infection. Accordingly, the appearance of the yeast LTA$_4$ hydrolase enzyme may signal the start of a pathogenic, non-commensal phase of Candida growth.

Thus, the present invention provides novel yeast LTA$_4$ hydrolase proteins. In a preferred embodiment, the yeast LTA$_4$ hydrolase proteins are from Candida strains, and in the preferred embodiment, from *C. albicans*. However, using the techniques outlined below, LTA$_4$ hydrolase proteins from other organisms may also be obtained. For example, a yeast-type LTA$_4$ hydrolase may be found in fungal strains, as is outlined below.

A yeast LTA$_4$ hydrolase protein may be defined and identified in several ways. A yeast LTA$_4$ hydrolase nucleic acid or yeast LTA$_4$ hydrolase protein is initially identified by substantial nucleic acid and/or amino acid sequence homology to the sequences shown in FIGS. 1 and 2 (SEQ ID NOS: 1–2). Such homology can be based upon the overall nucleic acid or amino acid sequence.

The yeast LTA$_4$ hydrolase proteins of the present invention have limited sequence homology to LtA$_4$ hydrolases produced by mammals such as humans and mice. On the amino acid level, the yeast LTA$_4$ hydrolase protein from *C. albicans* has an overall 39% homology with both the human and mouse LTA$_4$ hydrolase proteins.

As used herein, a protein is a "yeast LTA$_4$ hydrolase protein" if the overall homology of the protein sequence to the amino acid sequences shown in FIG. 1 (SEQ ID NO: 2) is preferably greater than about 50%, more preferably greater than about 60% and most preferably greater than 75%. In some embodiments the homology will be as high as about 90 to 95 or 98%. This homology will be determined using standard techniques known in the art, such as the Best Fit sequence program described by Devereux et al., *Nucl. Acid Res.* 12:387–395 (1984). The alignment may include the introduction of gaps in the sequences to be aligned. In addition, for sequences which contain either more or fewer amino acids than the protein shown in FIG. 1 (SEQ ID NO:2), it is understood that the percentage of homology will be determined based on the number of homologous amino acids in relation to the total number of amino acids. Thus, for example, homology of sequences shorter than that shown in FIG. 1 (SEQ ID NO:2), as discussed below, will be determined using the number of amino acids in the shorter sequence.

Yeast LTA$_4$ hydrolase proteins of the present invention may be shorter or longer than the amino acid sequence shown in FIG. 1 (SEQ ID NO:2). Thus, in a preferred embodiment, included within the definition of yeast LTA$_4$ hydrolase proteins are portions or fragments of the sequences shown in FIG. 1 (SEQ ID NO:2). The fragments may range from about 30 to about 500 amino acids. Fragments of at least about 50 amino acids are preferred and fragments of at least about 100 amino acids are particularly preferred.

In a preferred embodiment, when the yeast LTA$_4$ hydrolase protein is to be used to generate antibodies, for example as a vaccine or a diagnostic tool, the yeast LTA$_4$ hydrolase protein must share at least one epitope or determinant with the full length protein shown in FIG. 1 (SEQ ID NO:2). By "epitope" or "determinant" herein is meant a portion of a protein which will generate and bind an antibody. Thus, in most instances, antibodies made to a smaller yeast LTA$_4$ hydrolase protein, i.e. a fragment, will be able to bind to the full length protein. In this embodiment, the fragment need not be enzymatically active. In a preferred embodiment, the epitope is unique; that is, antibodies generated to a unique epitope show little or no cross-reactivity with other proteins such as the mouse or human LTA$_4$ hydrolase proteins.

Specifically included within the definition of "yeast LTA$_4$ hydrolase protein" are proteins which retain biological activity. As outlined above, the yeast LTA$_4$ hydrolase enzyme has two enzymatic activities, a LTA$_4$ hydrolysis activity and an aminopeptidase activity. In one embodiment, the yeast LTA$_4$ hydrolase enzyme has at least the LTA$_4$ hydrolyzing activity. In the preferred embodiment, the yeast LTA$_4$ hydrolase protein hydrolyzes all or most of the LTA$_4$ to a product which is less chemotactic for neutrophils; i.e. a less active, more non-polar leukotriene than LTB$_4$, such as 5,6 diHETE.

It is possible that the yeast enzyme does convert a small amount of LTA$_4$ to LTB$_4$, while yielding primarily the 5,6, diHETE product. As noted above, the identification of the major product of the yeast LTA$_4$ hydrolase enzyme is tentative; it is possible that the product has an unknown function in the inflammatory or immune response of the host. Thus, in a preferred embodiment, the product of the reaction of the yeast LtA$_4$ hydrolase enzymes of the present invention on LTA$_4$ is not LTB$_4$ but rather a different product, which is preferably a less potent proinflammatory compound. In an alternative embodiment, the yeast LTA$_4$ hydrolase enzyme has both the LTA$_4$ hydrolysis activity as well as the aminopeptidase activity. In a further embodiment, the yeast LTA$_4$ hydrolase has only either the aminopeptidase activity or the yeast LTA$_4$ hydrolase activity.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 2 (SEQ ID NO: 1) is preferably greater than 50%, more preferably greater than about 60% and most preferably greater than 80%. In some embodiments the homology will be as high as about 90 to 95 or 98%.

The nucleic acid sequences encoding the yeast LTA$_4$ hydrolase proteins of C. albicans have limited nucleic acid homology to the human and mouse sequences encoding the yeast LTA$_4$ hydrolase proteins. Specifically, the nucleic acid sequence encoding the yeast LTA$_4$ hydrolase protein from C. albicans has, at best, an overall 50% homology with the human and mouse nucleic acid encoding the yeast LTA$_4$ hydrolase protein.

In one embodiment, the nucleic acid homology is determined through hybridization studies. Thus, for example, nucleic acids which hybridize under high stringency to all or part of the nucleic acid sequences shown in FIG. 2 (SEQ ID NO:1) are considered yeast LTA$_4$ hydrolase protein genes. High stringency conditions are generally 0.1 XSSC at 65° C.

The yeast LTA$_4$ hydrolase proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments. Specifically included within the definition of nucleic acid are anti-sense nucleic acids. Generally, anti-sense nucleic acids function to prevent expression of mRNA, such that a yeast LTA$_4$ hydrolase protein is not made. An anti-sense nucleic acid will hybridize to the nucleic acid sequences shown in FIG. 2 (SEQ ID NO:1) or their complements, but may contain ribonucleotides as well as deoxyribonucleotides. The hybridization conditions used for the determination of anti-sense hybridization will generally be high stringency conditions, such as 0.1XSSC at 65° C.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated yeast LTA$_4$ hydrolase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production of a yeast LTA$_4$ hydrolase protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions.

Also included with the definition of yeast LTA$_4$ hydrolase protein are yeast LTA$_4$ hydrolase proteins from other organisms, which are cloned and expressed as outlined below. The yeast LTA$_4$ hydrolase nucleic acid sequences of FIG. 2 (SEQ ID NO:1) may be lined up with the human and mouse sequences and nonhomologous sequences may be selected for possible probe sequences as is known in the art. Of particular relevance is the nucleotide sequence encoding the yeast LTA$_4$ hydrolase residues alanine 332 to lysine 347, since the human protein is missing these residues. In addition, the nucleotide sequences encoding all or part of the amino acids at 1–130, and at 408–623 are useful, since the homology in these areas is very low.

In particular, other Candida strains, such as C. krusei, C. parapsilosis, C. tropicalis, C. psuedotropicalis, C. guilliermondii, C. rugosa, and C. lusitaniae, or other organisms such as Histoplasma capsulatum, Cryptococcus meoformans, Sporothrix schenkii, Blastomyces dermatitidis, Coccidioides immitis, and Aspergillus species may be probed for yeast LTA$_4$ hydrolase activity and proteins.

Once the yeast LTA$_4$ hydrolase protein nucleic acid is identified, it can be cloned and, if necessary, its constituent parts recombined to form the entire yeast LTA$_4$ hydrolase protein nucleic acid. Once isolated from its natural source, e.g., contained within a plasmid or other vector or excised therefrom as a linear nucleic acid segment, the recombinant yeast LTA$_4$ hydrolase protein nucleic acid can be further used as a probe to identify and isolate other yeast LTA$_4$ hydrolase protein nucleic acids. It can also be used as a "precursor" nucleic acid to make modified or variant yeast LTA$_4$ hydrolase protein nucleic acids and proteins.

Using the nucleic acids of the present invention which encode yeast LTA$_4$ hydrolase protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the yeast $LTA_4$ hydrolase protein. "Operably linked" in this context means that the transcriptional and translational regulatory DNA is positioned relative to the coding sequence of the yeast $LTA_4$ hydrolase protein in such a manner that transcription is initiated. Generally, this will mean that the promoter and transcriptional initiation or start sequences are positioned 5' to the yeast $LTA_4$ hydrolase protein coding region. The transcriptional and translational regulatory nucleic acid will generally be appropriate to the host cell used to express the yeast $LTA_4$ hydrolase protein; for example, transcriptional and translational regulatory nucleic acid sequences from Bacillus are preferably used to express the yeast $LTA_4$ hydrolase protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or yeast cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The yeast $LTA_4$ hydrolase proteins of the present invention are produced by culturing a host cell transformed with an expression vector containing nucleic acid encoding a yeast $LTA_4$ hydrolase protein, under the appropriate conditions to induce or cause expression of the yeast $LTA_4$ hydrolase protein. The conditions appropriate for yeast $LTA_4$ hydrolase protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae, Candida albicans* and other yeasts, *E. coli, Bacillus subtilis,* SF9 cells, C129 cells, 293 cells, Neurospora, BHK, CHO, COS, and HeLa cells, and immortalized mammalian myeloid and lymphoid cell lines.

In a preferred embodiment, yeast $LTA_4$ hydrolase proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of yeast $LTA_4$ hydrolase protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the yeast $LTA_4$ hydrolase protein in bacteria. The signal sequence typically encodes a signal peptide comprised of hydrophobic amino acids which direct the secretion of the protein from the cell, as is well known in the art.

The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, yeast $LTA_4$ hydrolase proteins are produced in insect cells. Expression vectors for the transformation of insect cells, and in particular, baculovirus-based expression vectors, are well known in the art and are commercially produced in kits.

Mammalian expression systems are also known in the art and are used in one embodiment. A mammalian promoter is any DNA sequence capable of binding mammalian RNA polymerase and initiating the downstream (3') transcription of a coding sequence for yeast $LTA_4$ hydrolase protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide(s) in liposomes, and direct microinjection of the DNA into nuclei.

In a preferred embodiment, yeast $LTA_4$ hydrolase protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant yeast $LTA_4$ hydrolase protein may be expressed intracellularly or secreted, or can be expressed at the cell surface. Without being bound by theory, it appears that the yeast $LTA_4$ hydrolase enzyme is secreted extracellularly. Thus, in a preferred embodiment, the yeast $LTA_4$ hydrolase enzyme is secreted.

The yeast $LTA_4$ hydrolase protein may also be made as a fusion protein, using techniques well known in the art. Thus, for example, for the creation of monoclonal antibodies, if the desired epitope is small, the yeast $LTA_4$ hydrolase protein may be fused to a carrier protein to form an immunogen. Alternatively, the yeast $LTA_4$ hydrolase protein may be made as a fusion protein to increase expression or facilitate purification.

Also included within the definition of yeast $LTA_4$ hydrolase proteins of the present invention are amino acid sequence variants. These variants fall into one or more of three classes: substitutional, insertional or deletional variants. These variants ordinarily are prepared by random or site specific mutagenesis of nucleotides in the DNA encoding the yeast $LTA_4$ hydrolase protein, using cassette mutagenesis or other techniques well known in the art, to produce DNA encoding the variant, and thereafter expressing the DNA in recombinant cell culture as outlined above. However, variant yeast $LTA_4$ hydrolase protein fragments having up to about 100–150 residues may be prepared by in vitro synthesis using established techniques. Amino acid sequence variants are preferably characterized by the predetermined nature of the variation, a feature that sets them apart from naturally occurring allelic or interspecies variation of the yeast $LTA_4$ hydrolase protein amino acid sequence which are generally included within the broad definition of yeast $LTA_4$ hydrolase proteins. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed yeast $LTA_4$ hydrolase protein variants screened for the optimal combination of desired activity. Techniques for making substitution mutations at predetermined sites in DNA having a known sequence are well known, for example, M13 primer mutagenesis. Screening of the mutants is done using assays of yeast $LTA_4$ hydrolase activities; for example, the variant yeast $LTA_4$ hydrolase protein may be expressed and its biological characteristics evaluated directly. For example, the ability of the variant to hydrolyze $LTA_4$ or act as an aminopeptidase may be assayed using the protocols outlined in the examples. Alternatively, mutated yeast $LTA_4$ hydrolase nucleic acids are placed in yeast $LTA_4$ hydrolase deletion strains and tested for yeast $LTA_4$ hydrolase activity, as disclosed herein. The creation of deletion strains, given a gene sequence, is known in the art. For example, nucleic acid encoding the variants may be expressed in a *C. albicans* strain deficient in the yeast $LTA_4$ hydrolase protein, and the $LTA_4$ hydrolyzing activity of the variant *C. albicans* evaluated.

Amino acid substitutions are typically of single residues at any one position, although as many as 35 may be substituted. Insertions usually will be on the order of from about 1 to 20 amino acids, although considerably larger insertions may be tolerated. Deletions range from about 1 to 30 residues, although in some cases deletions may be much larger, as for example when one of the domains of the yeast $LTA_4$ hydrolase protein is deleted.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the yeast $LTA_4$ hydrolase protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the yeast $LTA_4$ hydrolase proteins as needed. Alternatively, the variant may be designed such that the biological activity of the yeast $LTA_4$ hydrolase protein is altered. For example, the catalytic residue of the active site of the aminopeptidase activity, a glutamic acid at position 296, may be altered to decrease or eliminate enzymatic activity. Similarly, the residues involved in zinc binding, the histidine at position 295, the histidine at position 299, and the glutamic acid at position 318, may be altered to modify the metal binding of the enzyme, and thus the enzymatic activity.

In a preferred embodiment, the yeast $LTA_4$ hydrolase protein is purified or isolated after expression. Yeast $LTA_4$ hydrolase proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the yeast $LTA_4$ hydrolase protein may be purified using a standard anti-$LTA_4$ hydrolase antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the yeast $LTA_4$ hydrolase protein. In some instances no purification will be necessary.

Once expressed and purified if necessary, the yeast $LTA_4$ hydrolase proteins are useful in a number of applications.

For example, the yeast $LTA_4$ hydrolase proteins can be coupled, using standard technology, to affinity chromatography columns or other solid substrates. These columns may then be used to either diagnose the presence of C. albicans antibodies, and thus C. albicans infection in samples obtained from animals or patients exposed to the C. albicans organism, or to purify the antibodies. The purified antibodies may then be used as outlined below.

Full length yeast $LTA_4$ hydrolase proteins or fragments of yeast $LTA_4$ hydrolase proteins are also useful in diagnostic assays for the presence of yeast $LTA_4$ hydrolase proteins, and thus of C. albicans infection, such as radioimmunoassays and ELISAs, which use both yeast $LTA_4$ hydrolase protein antibodies and yeast $LTA_4$ hydrolase proteins. For example, competitive inhibition assays are well known in the art.

Additionally, the yeast $LTA_4$ hydrolase proteins are useful as immunogenic preparations, to make antibodies to yeast $LTA_4$ hydrolase proteins. These antibodies find use in a number of applications. In a preferred embodiment, the antibodies are used to diagnose the presence of an C. albicans infection in a sample or patient. This will be done using techniques well known in the art; for example, samples such as blood or tissue samples may be obtained from a patient and tested for reactivity with the antibodies. In a preferred embodiment, monoclonal antibodies are generated to the yeast $LTA_4$ hydrolase protein, using techniques well known in the art. As outlined above, the antibodies may be generated to the full length yeast $LTA_4$ hydrolase protein, or a portion of the yeast $LTA_4$ hydrolase protein which retains common epitopes with the full length protein. These monoclonal antibodies will bind to the yeast $LTA_4$ hydrolase; in a preferred embodiment, they bind to the full length protein.

Antibodies generated to yeast $LTA_4$ hydrolase proteins may also be used in passive immunization treatments, as is known in the art.

In one embodiment, the antibodies or proteins may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the yeast $LTA_4$ hydrolase protein antibody may be labelled for detection, or a secondary antibody to the yeast $LTA_4$ hydrolase protein antibody may be created and labelled.

In one embodiment, the antibodies generated to the yeast $LTA_4$ hydrolase proteins of the invention are used to purify or separate yeast $LTA_4$ hydrolase proteins or the C. albicans organism from a sample.

In a preferred embodiment, the yeast $LTA_4$ hydrolase proteins of the invention are used as vaccines for the prophylactic or therapeutic treatment of an C. albicans infection in a patient. By "vaccine" herein is meant an antigen or compound which elicits an immune response in an animal or patient. The vaccine may be administered prophylactically, for example to a patient never previously exposed to the antigen, or in an asymptomatic phase of Candida infection, such that subsequent infection by the *C. albicans* organism is prevented. Alternatively, the vaccine may be administered therapeutically to a patient previously exposed or infected by the *C. albicans* organism. While infection cannot be prevented, in this case an immune response is generated which allows the patient's immune system to more effectively combat the infection. Thus, for example, there may be a decrease or lessening of the symptoms associated with infection.

For example, women with recurrent vulvovaginal candidiasis may be innoculated or vaccinated during an asymptomatic phase to achieve protective immunity that would prevent or delay a recurrence of symptoms. Similar, patients scheduled for organ transplant may benefit from prophylactic immunization, to prevent the establishment of a systemic Candida infection when they are immunesuppressed.

A "patient" for the purposes of the present invention includes both humans and other animals and organisms which are subject to infection by *C. albicans*. Thus the methods are applicable to both human and animal therapy, and experimental animal models.

The administration of the yeast $LTA_4$ hydrolase protein as a vaccine is done in a variety of ways. Generally, the yeast $LTA_4$ hydrolase proteins can be formulated according to known methods to prepare pharmaceutically useful compositions, whereby therapeutically effectively amounts of the yeast $LTA_4$ hydrolase protein are combined in admixture with a pharmaceutically acceptable carrier vehicle. Suitable vehicles and their formulation are well known in the art. Such compositions will contain an effective amount of the yeast $LTA_4$ hydrolase protein together with a suitable amount of vehicle in order to prepare pharmaceutically acceptable compositions for effective administration to the host. The composition may include salts, buffers, carrier proteins such as serum albumin, targeting molecules to localize the yeast $LTA_4$ hydrolase protein at the appropriate site or tissue within the organism, and other molecules. The composition may include adjuvants as well.

In one embodiment, the vaccine is administered as a single dose; that is, one dose is adequate to induce a sufficient immune response to prophylactically or therapeutically treat a *C. albicans* infection. In alternate embodiments, the vaccine is administered as several doses over a period of time, as a primary vaccination and "booster" vaccinations.

By "therapeutically effective amounts" herein is meant an amount of the yeast $LTA_4$ hydrolase protein which is sufficient to induce an immune response. This amount may be different depending on whether prophylactic or therapeutic treatment is desired, and are determined using techniques well known in the art. The amounts may be adjusted if adjuvants are used.

In one embodiment, *C. albicans* deletion strains are created as outlined below. In this embodiment, the deletion strains are useful to generate antibodies to *C. albicans* organisms, which may be used in diagnostic assays as outlined above for the detection of *C. albicans* infection in a sample or patient. An alternative embodiment utilizes the deletion strain as a negative control in yeast $LTA_4$ hydrolase assays. The deletion strains are also useful to explore the role of this yeast $LTA_4$ hydrolase enzyme in the switch between commensal growth and pathogenic growth. For example, the deletion strain can be used to infect animal models to compare the progress of the infection with deletion strains with wild-type strains.

In a preferred embodiment, the deletion strain is deficient in yeast $LTA_4$ hydrolase; i.e. the strain does not express biologically active yeast $LTA_4$ hydrolase. Thus, for example, *C. albicans* strains are made which have the yeast $LTA_4$ hydrolase gene completely or partially deleted. If the gene is not completely deleted, the deletion is sufficient to eliminate biological activity of the proteins.

In a preferred embodiment, the gene for the yeast $LTA_4$ hydrolase protein is completely deleted, thus minimizing the chances of homologous recombination with a wild-type *C. albicans* organism. By "completely deleted" herein is meant that no nucleotides which encode amino acids of at least the mature protein remain in the genome of the host organism.

In an alternative embodiment, the gene for the yeast $LTA_4$ hydrolase protein is partially deleted. By "partially deleted" herein is meant that enough of the nucleic acid sequence is missing from the genome of the organism to result in a lack of biological activity. The partial deletion may be such that an inactive protein is expressed, or no protein is expressed.

The creation of deletion strains is well known in the art.

In an alternative embodiment, the deletion strains have mutations in the yeast $LTA_4$ hydrolase protein such that the biological activity of the yeast $LTA_4$ hydrolase is eliminated. The mutation may be either a substitution, insertion or deletion. These organisms are created using techniques well known in the art.

In an additional embodiment, the yeast $LTA_4$ hydrolase proteins of the present invention are useful to modulate or reduce an inflammatory response in a patient. Since $LTB_4$ is generated by the hydrolysis of $LTA_4$ by endogeneous mammalian $LTA_4$ hydrolase, addition of a yeast $LTA_4$ hydrolase enzyme which converts all or part of the endogeneous $LTA_4$ to a inactive or less potent proinflammatory agent than $LTB_4$ allows the proinflammatory response to be lessened or eliminated. Thus, in this embodiment, the yeast $LTA_4$ hydrolase is used to reduce the levels of either or both of the host's endogenous $LTA_4$ and $LTB_4$ levels. In a preferred embodiment, the levels of a less potent proinflammatory agent such as 5,6, diHETE are increased.

In this embodiment, the yeast $LTA_4$ hydrolase enzyme may be systemically or locally applied to decrease the inflammatory response of a patient. The therapeutically effective dose is determined according to the endogeneous levels of $LTA_4$ as is known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLE 1

Cloning and Expression of Yeast $LTA_4$ Hydrolase

RNA from Candida albicans grown in lab broth at 23 degrees and 37 degrees was isolated and $(dT)_{12-14}$ used as a primer in synthesis of cDNAs. The total cDNA pool was used as template in a PCR reaction with the primers $T_{12}AG$ (SEQ ID NO:3) and TAGCATATGGAG (SEQ ID NO:4). The PCR reaction generated a series of amplified fragments, each corresponding to a different cellular RNA. Amplified fragments found in reactions using RNA from the 23° C. culture, but not in reactions using RNA from the 37° C. culture were isolated and cloned. Sequence of one of these revealed homology to mammalian $LTA_4$ hydrolase.

The resulting cDNA fragment was sequenced using standard techniques. A genomic library was constructed from strain 5314, a clinical isolate obtained from William Fonzi at UCLA. The cDNA fragment was used as a probe, and a full length yeast $LTA_4$ hydrolase (hereinafter $cLTA_4H$) was cloned as a 6 Kb HindIII fragment. The full length coding region was sequenced on both strands, using the standard dideoxy method. The sequence of the gene (SEQ ID NO:1) is shown in FIG. 2.

A restriction site was introduced just upstream of the initiation codon, and a fusion protein was constructed with glutathione-s-transferase (GST) (pGEXIIKG, Pharmacia) which contains a thrombin cleavage site. The fusion protein was overexpressed in *E. coli* strain DH12S (Gibco BRL) under an IPTG inducible promoter, and the fusion protein purified by binding to glutathione sepharose (Pharmacia). The purified protein was cleaved from the sepharose beads by treatment with thrombin, and purified away from the GST/sepharose by centrifugation. The resulting protein was >95% pure as assayed by SDS-PAGE and staining by commasie blue. As a control, the GST moiety of the fusion protein was overexpressed alone in DH12S and purified in parallel.

The purified recombinant cLTA4H was subjected to two functional tests. The mammalian homolog of cLTA4H has two distinct enzymatic functions; it can hydrolyze $LTA_4$ to $LTB_4$, and in addition can cleave small peptides non-specifically (aminopeptidase activity). The aminopeptidase activity was tested by incubating the enzyme in PBS with L-ala-p-nitroanalide, the hydrolysis of which yields p-nitroanalide which can be detected spectrophotometrically at 405 nM. cLTA4H showed significant aminopeptidase activity, as shown in FIG. 3. No activity was detected in the mock GST alone extract, despite its high expression; this indicated that the observed activity is due to cLTA4H and not to an impurity or artifact of the purification.

The enzymatic activity against $LTA_4$ was also evaluated. Since $LTA_4$ is hydrolyzed rapidly at neutral pH, we had to separate enzymatic from non-enzymatic products of $LTA_4$ hydrolysis. This was done using a $C_{18}$ reverse phase chromatography column, with isocratic elution with methanol/water/acetic acid (48/52/0.1%). Retention times from the products of enzymatic and non-enzymatic hydrolysis are shown in FIG. 4. $LTA_4$ methyl ester was purchased from Cayman Chemicals, saponified (according to manufacturer's instructions) in acetone/NaOH to give the free acid. This was diluted directly into PBS supplemented with 10 mg/ml BSA and enzyme if any. The reaction was stopped at 5 minutes by acidification to pH 4 with HCl, acetone (1 volume) and PGB2 was added as an internal standard. Equivalent portions of the reactions were chromatographed and the absorbance recorded at 415 nM. Hydrolysis of $LTA_4$ by cLTA4H yielded a major peak that cochromatographed with 5(S),6(R) diHETE, and a minor peak that chromatographs with $LTB_4$. The identity of these products remains to be rigorously shown.

We claim:

1. A recombinant nucleic acid encoding a yeast Leukotriene $A_4$ ($LTA_4$) hydrolase protein.

2. A recombinant nucleic acid according to claim 1 which has a sequence homologous to the sequence of SEQ ID NO:1.

3. A recombinant nucleic acid according to claim 1 which has the sequence of SEQ ID NO:1.

4. An expression vector comprising transcriptional and translational regulatory DNA operably linked to DNA encoding a yeast $LTA_4$ hydrolase protein.

5. A host cell transformed with an expression vector comprising a nucleic acid encoding a yeast $LTA_4$ hydrolase protein.

6. A method of producing a yeast $LTA_4$ hydrolase protein comprising:

a) culturing a host cell transformed with an expression vector comprising a nucleic acid encoding a yeast $LTA_4$ hydrolase protein; and b) expressing said nucleic acid to produce a yeast $LTA_4$ hydrolase protein.

7. A recombinant nucleic acid capable of hybridizing under high stringency conditions to all or part of SEQ ID NO:1.

\* \* \* \* \*